(12) United States Patent
Horn

(10) Patent No.: US 7,534,619 B2
(45) Date of Patent: May 19, 2009

(54) METHOD FOR DETERMINING METABOLIC TYPE

(76) Inventor: Brandon Horn, 160 E. Corson St., #129, Pasadena, CA (US) 91103

( * ) Notice: Subject to any disclaimer, the term of this patent is extended or adjusted under 35 U.S.C. 154(b) by 286 days.

(21) Appl. No.: 11/588,761

(22) Filed: Oct. 27, 2006

(65) Prior Publication Data

US 2007/0099302 A1 May 3, 2007

Related U.S. Application Data

(60) Provisional application No. 60/731,016, filed on Oct. 27, 2005.

(51) Int. Cl.
*G01N 33/50* (2006.01)
*G01N 33/84* (2006.01)

(52) U.S. Cl. .............. 436/68; 436/63; 436/163; 436/183

(58) Field of Classification Search .......... 436/63, 436/68, 95, 163, 183
See application file for complete search history.

(56) References Cited

U.S. PATENT DOCUMENTS

| | | | |
|---|---|---|---|
| 5,122,362 A | 6/1992 | Phillips et al. | |
| 5,603,817 A | 2/1997 | Settler et al. | |
| 2003/0091975 A1* | 5/2003 | Leyland-Jones | 435/4 |
| 2005/0074745 A1 | 4/2005 | Clayton et al. | |

OTHER PUBLICATIONS

Internet article from http://www.newconnexion.net/article/01-03/metabolic.html, entitled Metabolic Typing: The Key to Normalizing Weight and Improving Metabolism, Jan. 2003, pp. 1-2.*

* cited by examiner

*Primary Examiner*—Maureen M Wallenhorst
(74) *Attorney, Agent, or Firm*—Christie, Parker & Hale LLP

(57) ABSTRACT

A method for determining a person's metabolic typing. The method includes the steps of taking a baseline reading to determine a person's blood pH, administering a substance challenge to a person to determine how the substance affects the person's blood pH, waiting a period of time, retaking the person's blood ph, and from any difference in the baseline reading and post-challenge reading, determining if the patient's blood has been alkalized or acidified by the substance challenge in order to determine the person's metabolic type. The invention is also a method to test the blood pH shifting effects of substances on people of different metabolic types, by determining whether the substance will cause the blood of persons having known metabolic types to become more acidic or alkaline.

18 Claims, 1 Drawing Sheet

1. Condensation
2a. Dehydration
2b. Hydration
3. Oxidative decarboxylation
4. Oxidative decarboxylation
5. Substrate level phosphorylation
6. Dehydrogenation
7. Hydration
8. Dehydrogenation

METHOD FOR DETERMINING METABOLIC TYPE

CROSS-REFERENCE TO RELATED APPLICATION(S)

This application claims priority to and the benefit of U.S. Provisional Application No. 60/731,016, filed on Oct. 27, 2005, which is incorporated by reference as if set forth in full herein.

BACKGROUND

The invention relates to variances in how people metabolize substances and the effects this can have on the blood. Historically, this concept has been applied to nutrition through a process called metabolic typing. Metabolic typing has been used to help individualize nutrition. The hypothesis of metabolic typing is that there are individual variances in metabolism that preclude the application of a single diet that is healthy for everyone.

Metabolic typing looks at the inter-relationship of two of the body's major systems relating to the production and processing of energy: the autonomic nervous system (ANS) and the oxidative system (OS). The theory is that one system predominates at a given time in an individual and determining which system predominates will allow you to establish their ideal diet.

In many industrialized nations, the incidence of obesity and illness such as diabetes, cancer and other diseases have been steadily rising over the past few decades despite increased spending on health care and the prevalence of more and more specialty diet foods. Indeed, people are bombarded with conflicting messages about the right way to eat, including eating for one's blood type, vegetarianism, juice diets, high protein/high fat diets, low-fat diets, raw foods diets, to name just a few diet philosophies. Some people go from diet to diet trying to find something that works, and oftentimes give up frustrated.

It has become apparent that people have different dietary needs and no single universal diet is right for everyone. Just as people can look very different on the outside, how their body processes food and nutrients can also greatly differ. Indeed, it is becoming more accepted that while some people thrive on a high protein low carbohydrate diet, others do better on a high complex carbohydrate diet with lower amounts of protein.

In order to understand metabolic typing, it is important to understand some basic interrelationships between blood pH, the nervous system, respiration and the Krebs cycle.

In the past, the relationship between the blood pH (relative alkalinity or acidity of venous blood) and relative health has been examined. Venous blood pH ranges from a low of about 7.24 to a high of about 7.65. Metabolic Typing practitioners propose that the ideal venous pH is 7.46 and even the slightest variance from this is pathological. If the actual pH is lower than 7.46 the blood is termed "acidic" and if it is above 7.46 it is termed "alkaline".

The nervous system is divided into two parts: the cerebrospinal division and the autonomic division. The cerebrospinal division is more for voluntary activities whereas the autonomic nervous system is more for involuntary activities (such as heart rate, digestion, respiration, tissue repair, etc.)

The autonomic system exerts a regulatory effect on the general operation of the organism. As such, it serves as a major homeostatic control mechanism. It has two efferent neurons in series between the central nervous system and the innervated organ. Through this innervation, it influences the rate of metabolism, muscle tone of the viscera, blood flow, and other aspects of general homeostasis. The actions of the autonomic division are duplicated by various hormones, such as epinephrine, and drugs, such as acetylcholine.

The autonomic nervous system is sub-divided into two branches: parasympathetic and sympathetic. Each branch regulates a different set of metabolic activities.

The parasympathetic branch consists of two neuron chains, but differs from the sympathetic nervous system in that the first neuron has a long axon and synapses with the second neuron either near or in the organ innervated. The parasympathetic system appears to be in control during such pleasant periods as digestion and rest.

The sympathetic system, on the other hand, can alter the level at which various organs function, enabling the body to rise to emergency demands encountered in situations involving flight, combat, pursuit, and pain. In general, its action is in opposition to that of the parasympathetic nervous system. However, it cannot be stated that one is excitatory and the other is relaxing. It depends which organs one is referring to.

The dualistic, or push-pull phenomenon of the two branches is what enables them to work together in a synchronized manner to regulate all involuntary metabolic processes in the body. For example, the sympathetic system speeds up heart rate while the parasympathetic system slows it down. However, in the case of other involuntary functions, the roles can be reversed. For instance, the parasympathetic system activates the secretion of stomach acid and contraction of the stomach muscles to initiate digestion, whereas the sympathetic system can shut it down.

It is hypothesized that most people are neurologically influenced more strongly by either the sympathetic or parasympathetic system. People also vary in the degree by which the respective systems influence them. Possibly as a result of inherited or environmentally acquired differences, people have different physical, psychological and behavioral characteristics that correlate with either a "sympathetic dominance" (fight or flight) or a "parasympathetic dominance" (rest and digest.) It has been found that some foods and nutrients stimulate or strengthen one of the branches while having the opposite effect on the other.

The processes by which we convert food into energy is quite complex. Inside each of our cells (except mature red blood cells) are tiny oval-shaped organelles known as mitochondria. These organelles range in number from about 300 in fat cells to 4,000 in heart cells. The mitochondria are often referred to as the body's energy furnaces because they convert nutrients into energy. This happens primarily through a complex set of interactions known as the Krebs cycle.

FIG. 1 is a simplified representation of the Krebs cycle. Essentially, the Krebs cycle involves a series of enzymatic reactions that transform carbohydrates (as glucose, then pyruvate) into intermediate substances. Proteins, in the form of their constituent amino acids, are broken down and fed into the cycle at different points. Fats (as fatty acids) are split into smaller compounds known as ketones or ketone bodies through a process known as beta-oxidation. These ketones are then further broken down into acetyl-CoA (acetyl coenzyme acetate), where they enter the top of the Krebs cycle.

The primary substrates, or raw materials, for the Krebs cycle are glucose (extracted from carbohydrate foods) and the end-products of fatty acid metabolism, assisted by amino acids. Most of the glucose travels down the "left" side of the Krebs cycle (after first being transformed into pyruvate) to form a compound called oxaloacetate, while the remaining glucose combines with the fatty acids and amino acids to form acetyl CoA, which then travels down the "right" side of the cycle. These substances are then further spun around the Krebs cycle with the help of additional amino acids, various enzymes, and organic acids. In back-and-forth biochemical transmutations, acetyl CoA reacts with oxaloacetate to produce citrate (citric acid), which then reconverts back into oxaloacetate until the coenzyme intermediates are shuttled out the bottom of the Krebs cycle into the electron transport chain to complete the production of ATP energy. The intermediates so produced (the coenzymes NADH and FADH2) are then passed into the electron transport chain where they undergo a further series of reactions. These reactions involve both receiving and donating electrons down the chain-to-produce energy in the form of ATP (adenosine triphosphate) and water. The presence of sufficient oxygen within the cells is essential to the success of this procedure, and, accordingly, it is known as the oxidative process (after which the Oxidative system is named).

If insufficient oxygen is being delivered to the cells the entire process will be compromised. This is generally caused by an overly acidic venous blood pH or to an insufficiency of the enzyme (2-3 DPG) required to release oxygen from red blood cells. Another factor that compromises the efficient production of energy is an imbalance of raw materials fed to either "side" of the Krebs cycle.

As mentioned earlier, metabolic typing theory suggests that there are two main categories of people. These two categories are those whose energy is primarily influenced by the autonomic nervous system (Autonomic Types) and those influenced primarily by the oxidative system (Oxidative Types). Each of these two categories has subcategories that require different nutritional intake to maximize energy output. The so-called "Fast Oxidizers" tend to burn up glucose too rapidly. This requires a higher concentration of proteins and fats to be fed into the Krebs cycle to slow down the rate of glucose combustion. Conversely, "Slow Oxidizers" do not burn up glucose rapidly enough and require a higher percentage of glucose (and less protein and fats). If either of the Oxidative types eats a diet that is inappropriately weighted in the wrong direction, the result is insufficient energy (ATP) production and metabolic imbalance. Because ATP is needed to carry out all of our biological functions, this can have far-reaching consequences. For example, ATP is one of the primary factors in protein synthesis. Protein synthesis is necessary to manufacture enzymes that are necessary catalysts for every single biochemical reaction in the body: from digestion and the production of neurotransmitters and hormones, to immune function, tissue growth and DNA repair.

Some theorize that impaired energy production is a central malfunction that underlies chronic disease. Thus, the wrong "fuel mix" for one's Metabolic Type can have far-reaching consequences, and it is precisely these negative consequences that Metabolic Typing is seeking to avoid.

The other side to the oxidative process is the delivery of oxygen to the mitochondria. When we breathe in, the inhaled oxygen ($O_2$) is picked up in the lungs by the hemoglobin molecules and then is released to all the tissues of the body. The hemoglobin then picks up carbon dioxide ($CO_2$) and is exhaled. While oxygen is vital to support all life in the cells, the carbon dioxide is also vital, and serves as a catalyst that allows oxygen to be released from the hemoglobin. Indeed, the tissues require approximately three times as much carbon dioxide as they do oxygen. When the ratio of oxygen to carbon dioxide is correct, not only is oxygen more efficiently released to cells, but the blood vessels are more relaxed, edema is prevented, waste products are more efficiently eliminated, and energy production is optimized.

Oxygen in the body is alkaline forming and carbon dioxide is acid forming. If there is excess oxygen (or a deficit of carbon dioxide) the blood will be overly alkalized. Conversely, if there is an excess of carbon dioxide (or a deficit of oxygen) the blood will be overly acidified. This process is used in current protocols to help determine an individual's metabolic type. It is done by taking a series of baseline readings and then administering a glucose challenge drink. The drink is acid forming to the two oxidative types, thereby increasing their blood levels of carbon dioxide and decreasing their levels of oxygen. This has the effect of causing a relative increase in respiration rate as the body tries to compensate by breathing in more oxygen, while decreasing the ability to hold the breath (due to a deficit of oxygen). Individuals who demonstrate these and other related traits during the testing procedure will generally be the oxidative types.

In contrast, the glucose challenge drink is alkalizing to the autonomic types, thereby increasing blood levels of oxygen and decreasing their levels of carbon dioxide. Accordingly, their respiration will tend to react in the opposite way due to the presence of adequate amounts of oxygen. Therefore, their respiration rate decreases and their ability to hold their breath increases.

It is known that the rate at which the body metabolizes, or oxidizes, nutrition in food will determine whether a person is a fast oxidizer or a slow oxidizer. Taking venous blood and measuring its pH is one way that has been used to measure this. Individuals who operated primarily under the influence of the oxidative system could be characterized as fast oxidizers if they had relatively acidic blood or slow oxidizers if they had relatively alkaline blood. In contrast, in the Autonomic Types, relatively acidic blood would be called "sympathetic dominance" and relatively alkaline blood would be labeled "parasympathetic dominance".

Because of the aforementioned variances in metabolism, the same food can have opposite effects on different people. A food or nutritional supplement that acidifies one person's system may alkalinize another's. Thus, one ideally should know one's metabolic type in order to find out what constitutes a well-balanced diet for that person. Not knowing one's metabolic type makes it difficult at best to know which foods or nutrients are best for each person.

Metabolic typing also shows why nutrition should not be used in a generalized fashion—giving a certain nutrient for a certain condition. Instead, for more consistent, reliable success, one must address the particular nutritional requirements of each person.

DETAILED DESCRIPTION

Figure 1:
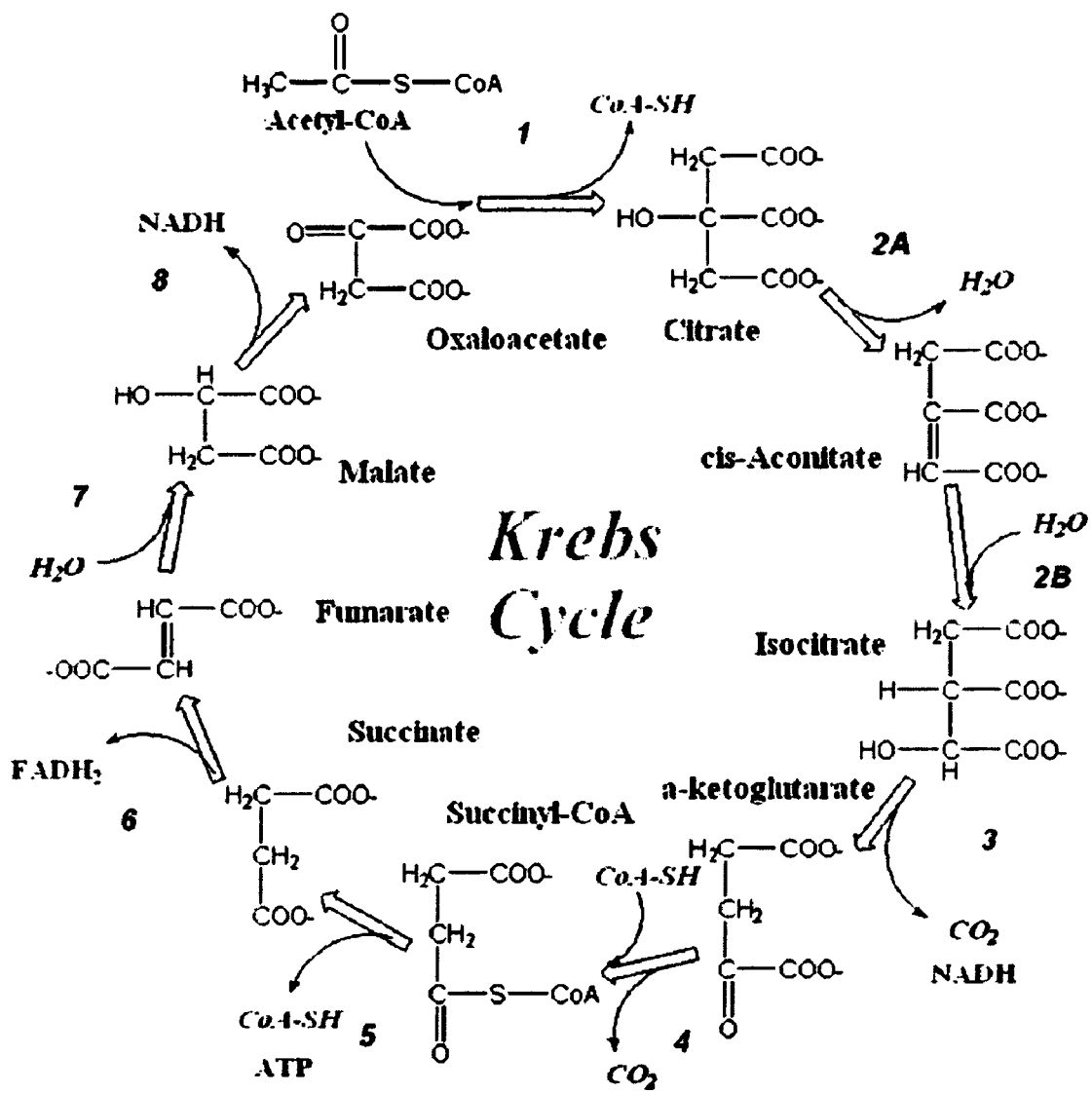
FIG. 1 is a simplified graphical representation of the Krebs (or citric acid) cycle.

In order to carry out the method of the invention, a practitioner will get a baseline reading by taking a measurement of venous (or arterial) blood pH (e.g. circulating blood) or otherwise measuring the concentrations of hydrogen or other gases in the blood or breath such as $CO_2$ or $O_2$. This is preferably from a patient who has fasted (no food or non-water beverages) for 2 to 12 hours or more (e.g., up to about 24 hours) in order to measure gas or ion concentration that is not influenced by the most recent meal or beverage and from which relative changes in alkalinity or acidity can be later measured.

If a blood sample is taken, it is collected and processed in a conventional manner (by venous or arterial blood draw, centrifuged or not depending on the method used, etc.) to determine the venous (or arterial) blood Ph (usually plasma), such as by use of a pH meter.

Following the baseline reading, a dose of glucose or other pure substance is administered either orally, transdermally, intravenously, via suppository, etc. After the glucose (or other substance) has been absorbed (the time depending on the type of substance used and method of administration), the blood pH or gas will be remeasured using the same method as measured during the baseline reading. A typical post-challenge pH reading may be taken anywhere from about 3 to about 60 minutes, again depending on the substance used and its absorption time into the blood stream.

By this step, the practitioner will be able to readily determine if the blood is being acidified or alkalized by the challenge substance.

Although glucose is preferable to use as a challenge because it tends to be absorbed into the blood stream fairly rapidly and consistently for most people, other pure substances (e.g., dextrose, vitamins, minerals, chemicals, pharmaceuticals, etc.) may be used as well and might be better suited for certain types of people such as diabetics. Preferably, the substance is a pure substance with constant and known characteristics. One way to administer a challenge is to have the patient drink a glass of water with the substance dissolved therein. The amount of the substance will depend on the type of substance, but one example would be to administer 50 grams of glucose diluted in 355 ml (12 ounces) of distilled water.

This invention is an improvement over prior attempts to determine one's metabolic type for the following reasons:

1. Prior attempts at measuring blood pH to determine one's metabolic type were done after the administration of a meal and over much longer periods of time. Because food is a complex, non-standardized substance, many variations in foods or people's digestive capacities could adversely affect the accuracy of the results. In addition, it took much longer to complete the process, anywhere from hours to days. This invention will greatly decrease the total time and greatly increase the accuracy of the measurements used to determine one's metabolic tendencies.

2. Prior attempts at determining metabolic type with a modified glucose challenge (glucose with potassium) sought to determine the blood pH circumstantially through a series of tests, many of which were either subjective or in part under voluntary control of the subject, and none of which were sufficiently accurate to be utilized alone. This prior method often produced conflicting or inconclusive results. The present invention improves upon the prior attempts by utilizing a pure substance to "challenge" the subject and directly measuring either blood pH or other independently accurate markers to produce rapid, objective, unambiguous, reproducible results.

The rate at which the body metabolizes, or oxidizes, nutrition in food will determine whether a person is a fast oxidizer or a slow oxidizer. Measuring the blood's pH is one way that has been used to measure this. Individuals who operated primarily under the influence of the oxidative system are characterized as fast oxidizers if they had relatively acidic blood or slow oxidizers if they had relatively alkaline blood. In contrast, in the Autonomic Types, relatively acidic blood would be called "sympathetic dominance" and relatively alkaline blood would be labeled "parasympathetic dominance".

The Determination of Metabolic Type

It is known that glucose acidifies the blood of people with oxidative types of metabolisms, and alkalizes the blood of people with autonomic types of metabolisms. It is also known that fast oxidizers and sympathetics have acidic baselines where slow oxidizers and parasympathetics have alkaline baseline readings. Therefore, we have four possibilities:

1. Baseline blood pH is acidic:
   a. Glucose challenge acidifies: Fast oxidizer
   b. Glucose challenge alkalizes: Sympathetic
2. Baseline blood pH is alkaline:
   a. Glucose challenge acidifies: Slow Oxidizer
   b. Glucose challenge alkalizes: Parasympathetic For blood gas and breath levels, studies can be done to determine the optimal concentration from which relatively high or low readings can be determined.

EXAMPLE 1

Patient A has a baseline venous pH of 7.42.

Five minutes after administration of a glucose challenge, his pH increases to 7.43. Because Patient A had an acidic pH that was alkalized by the glucose challenge his metabolic type is a Sympathetic metabolic type.

It is known that in some proportion of the population, whether they are an oxidative type or autonomic type can be influenced by various internal and external factors such as stress, circadian rhythms, environmental factors, etc. Therefore, the test can be conducted at different times of the day, month, year, location, etc.

Given the biodiversity that exists in people, it is likely that there will be different "ideal" blood pH levels or blood chemistries at which different persons will feel best and thrive. For example, it is possible to conduct the test during a time when a person feels great, and determine the pH. As such, acidity or alkalinity will be relative to that person's optimal blood pH, rather than a standardized 7.46.

Also, it is possible that for certain disease states and conditions that the "ideal" pH may be shifted. For example, some evidence suggests it may be more beneficial for some people with cancer to strive for a more alkaline pH. This method can then be used to help achieve the ideal pH relative to individual disease states.

In addition to just using the test to determine whether a certain challenge substance (e.g., glucose challenge) makes a person's blood more acid or alkaline, the test can be used to determine to what degree the substance affects a person's blood pH. For instance, the test could include various levels of affect or gradation so that instead of just saying a substance would make a person's blood more acidic or more alkaline, the degree of the change could be categorized. For example, certain substances could be determined to be highly acidifying or alkalizing, in which case, for certain people, the substance might be determined to be inappropriate, or appropriate with the addition of other substances to correct the blood pH.

This method can also be used to test out any substances on people who clearly fall within a particular metabolic type. For example, the method can be used to test herbs, supplements, foods, chemotherapeutic agents, pharmaceuticals, etc. This will allow doctors to choose the most appropriate medications for people and minimize side effects (in fact people should start feeling much better on medications that balance out their blood pH). For example, it might be determined that a certain drug shifts the blood pH to be more acid for one metabolic type and makes it more alkaline for the other metabolic type. In this case, a health care practitioner could then determine which drug is most appropriate for a given patients based on which appropriate drug has the most beneficial effect on the pH. This method could also be used to let a patient know when to switch medications.

Ideally, before drugs and supplements are given, the drug and supplements can be tested for how it shifts the blood pH and characteristic in different metabolic types, so that the drug can be typed, and any additional additives or agents can be used as required. It can even be tested on that particular individual.

The invention further provides a method to test the blood pH shifting effects of a substance on a person of a given metabolic type, comprising determining whether the substance will cause the blood of the person having a known metabolic types to become more acidic or more alkaline. Indeed, the method can be used to test substances comprising herbs, supplements, foods, chemicals, and/or pharmaceuticals to determine whether the tested substances are appropriate for certain metabolic types.

Although embodiments of the present invention have been described in detail hereinabove in connection with certain exemplary embodiments, it should be understood that the invention is not limited to the disclosed exemplary embodiments, but, on the contrary is intended to cover various modifications and/or equivalent arrangements included within the spirit and scope of the present invention.

I claim:

1. A method for metabolic typing, comprising:
   determining a baseline pH level of a person's blood;
   administering a pure substance with constant and known chemical characteristics as a substance challenge to said person to determine how the substance affects the person's blood pH level;
   waiting a period of time;
   redetermining the person's blood pH level post substance challenge; and
   from any difference in the baseline blood pH level reading and post-challenge blood pH level reading, determining if the person's blood has been made more alkaline or more acidic by the substance challenge in order to determine the person's metabolic type, and wherein when the baseline blood pH level is acidic, the substance challenge acidifies the blood of predominately fast oxidizers and alkalizes the blood of predominately sympathetic types, and wherein when the baseline blood pH level is alkaline, the substance challenge acidifies predominately slow oxidizer and alkalizes the blood of predominately parasympathetic types.

2. The method of claim 1, wherein the substance challenge is administered by having the patient drink a glass of water with the substance dissolved therein.

3. The method of claim 1, wherein the substance comprises one of glucose, dextrose, vitamins, minerals, or a pharmaceutical product.

4. The method of claim 1, wherein the substance is glucose, and about 50 grams of glucose is diluted in about 350 ml of pure water.

5. The method of claim 1, wherein the baseline blood pH level is taken in person who has fasted for about 2 to 24 hours.

6. The method of claim 1, wherein the baseline blood pH level is determined by taking a sample of the person's circulating blood and measuring its pH.

7. The method of claim 1, wherein the pH blood levels are measured with a pH meter.

8. The method of claim 1, wherein the baseline blood pH level is determined by extrapolating from the concentrations of hydrogen or other gasses in the blood or breath.

9. The method of claim 1, wherein the substance is administered one of orally, transdermally, intravenously, and/or via suppository.

10. The method of claim 1, wherein the period of time is about 3 minutes to about 60 minutes.

11. The method of claim 1, wherein the same method used to determine the baseline blood pH is used to redetermine the blood pH post substance challenge.

12. The method of claim 1, wherein the method can be conducted at different times of the day, month, year, and/or locations to determine the effect different times and/or location have on the person's metabolic type.

13. The method of claim 1, wherein the degree to which the substance challenge changes a person's blood pH is determined.

14. A method to test the blood pH shifting effects of a pure substance with constant and known chemical characteristics on people of different known metabolic types, comprising determining a baseline blood pH level of persons having known metabolic types; administering a pure substance with constant and known chemical characteristics as a substance challenge to said persons; waiting a period of time; redetermining each person's blood pH level post substance challenge; and determining whether the pure substance causes the blood of the persons having known metabolic types to become more acidic or more alkaline.

15. The method of claim 14, wherein the method is used to test the pure substance, which comprises or is derived from herbs, supplements, foods, chemicals, and/or pharmaceuticals, to determine whether the tested substance is appropriate for people of certain metabolic types.

16. The method of claim 14, wherein the pH shifting effects of the pure substance is determined in a particular person in order to decide whether that substance is appropriate for that particular person.

17. A method to test the blood pH shifting effects of a pure substance with constant and known chemical characteristics on a person of an already known metabolic type, comprising determining a baseline blood pH level of a person having an already known metabolic type; administering a pure substance with constant and known chemical characteristics as a substance challenge to said person; waiting a period of time; redetermining the person's blood pH level post substance challenge; and determining whether the pure substance causes the blood of the person having a known metabolic type to become more acidic or more alkaline.

18. The method of claim 17, wherein the method is used to test the pure substance, which comprises or is derived from herbs, supplements, foods, chemicals, and/or pharmaceuticals, to determine whether the tested substance is appropriate for a person of a certain metabolic type.

* * * * *